(12) United States Patent
Jacobs et al.

(10) Patent No.: US 6,896,518 B2
(45) Date of Patent: May 24, 2005

(54) TEETH TREATMENT DEVICE

(76) Inventors: Scott Jacobs, 12105 W. Cedar Ave., Lakewood, CO (US) 80228; Robert Ibsen, 1571 E. Main St., Santa Maria, CA (US) 93454

( * ) Notice: Subject to any disclaimer, the term of this patent is extended or adjusted under 35 U.S.C. 154(b) by 40 days.

(21) Appl. No.: 10/185,087

(22) Filed: Jun. 28, 2002

(65) Prior Publication Data

US 2004/0002035 A1 Jan. 1, 2004

(51) Int. Cl.[7] .............................. A61C 5/00; A61C 17/00
(52) U.S. Cl. ......................................... 433/215; 433/80
(58) Field of Search ........................ 433/80, 215, 216; 128/859, 860, 861, 862; 424/49, 53

(56) References Cited

U.S. PATENT DOCUMENTS

| | | | | |
|---|---|---|---|---|
| 5,730,592 A | * | 3/1998 | Meyer | 433/39 |
| 5,989,569 A | * | 11/1999 | Dirksing et al. | 424/401 |
| 2002/0006387 A1 | * | 1/2002 | Sagel et al. | 424/53 |
| 2003/0003421 A1 | * | 1/2003 | Bestenheider et al. | 433/215 |

* cited by examiner

*Primary Examiner*—Cary E. O'Connor
(74) *Attorney, Agent, or Firm*—John S. Munday

(57) ABSTRACT

A dental tray for treating teeth using upper and lower jaw patterns formed from dental wax. The patterns are thin, ranging from about 0.02 to 0.08 inches thick, with 0.04 inches preferred. The wax is capable of softening at body temperature. The patterns include a fold line formed along their lengths so an outer portion extends from the fold line about the length of the average person's front teeth, for example, about 0.625 inches. The inner portion is slightly smaller, for example, about 0.375 inches. The inner portions have gaps to permit the folded pattern to fit inside the patient's mouth. The inside of the tray may be textured to assist in holding bleaching material. The tray can be reused, and it is suitable for bleaching, fluoride treatment, stain removal, and other conventional dental procedures.

26 Claims, 1 Drawing Sheet

TEETH TREATMENT DEVICE

FIELD OF THE INVENTION

The present invention relates to making a dental tray customized to an individual patient's teeth, without the necessity of professional service, and the method to customize the dental tray. More particularly, the invention relates to the use of simple wax materials to allow individuals to brighten or bleach their own teeth without visiting a dental office or laboratory. Other conventional treatments are also contemplated.

BACKGROUND OF THE INVENTION

Dental trays are receptacles that are used to carry a medicine or dental hygiene materials, such as bleaching agents or fluoride application, and apply them to the teeth. It confines the material next to the teeth during the application. Bleaching is becoming more popular with the general public because efforts have been made to simplify the bleaching process and provide devices useful for home care and treatment by individuals without professional supervision There are two types of dental trays: stock and customized. Stock trays are pre-fabricated into a variety of standard sizes. They are used only for preliminary procedures and to produce impressions for casting as an interim step to creating more accurate dental trays and models of teeth. Custom trays are made by a dentist or technician by molding a material over a gypsum model of the patient's teeth. In order to get the gypsum model a preliminary impression is made from the patient's teeth. The model requires at least one dental visit and requires a laboratory to construct the gypsum model.

Once the model is made, the customized dental tray is formed by the dentist or lab according to the limitations of the materials to be used for the tray. If the tray is made of thermoplastic sheets, the tray may be formed in a vacuum forming machine or other machine which exerts pressure. The sheets are placed in a soft state over the model and pressure is applied while the material sets.

Attempts have also been made to design simpler devices for use by the patient at home. Tarvis U.S. Pat. No. 5,340,314 discloses the simplest use of dental wax, where the flat wax 14 in FIG. 2 is rolled to fit the shape of a dental plate. No suggestion of any use other than to take impressions is made in this patent Sintov et al U.S. Pat. No. 5,425,953 discloses a liquid polymer that includes a bleaching agent or other treatment agent. There is no reference to dental wax in Sintov et al. Curtis et al U.S. Pat. No. 5,639,445 employs a dilatant silicone polymer composition that is shaped and pressed against the teeth for sufficient time to release the active component. The polymer in Curtis et al is elastic, putty-like in composition, and is primarily directed at removing food particles from between the teeth and/or applying a dentifrice or medicament to below the gum line. Yarborough U.S. Pat. No. 5,713,738 employs laser light to activate bleaching agents applied to the teeth Latex rubber is used to cover the mouth other than the teeth.

Sagel et al U.S. Pat. No. 5,879,691 (Sagel '691) covers a delivery system using a strip of material having a low flexural stiffness. The material is generally characterized as being thin, having a flexural stiffness less than a predetermined value, readily conformable without permanent deformation, and having some adhesive properties. The preferred material is a gel and the specific preferred gel is formed from 70% glycerin, 5% carboxypolymethylene, 10% carbamide peroxide and 15% water. The material is very soft, almost mushy, and is different in kind from the dental wax which fractures when bent quickly at room temperature.

Sagel et al U.S. Pat. No. 5,891,453 (Sagel '453) discloses an improvement on Sagel '691, in which the strip of material is any number of materials, both synthetic and natural and would broadly include dental wax if that material, not disclosed, was as flexible as called for by the patent. The clear plastic flexible material on to which the gel is placed is much more flexible than dental wax.

Finally, Sagel et al U.S. Pat. No. 5,894,017 (Sagel '017) discloses the same flexible material with a substance on it for treating teeth. This patent calls for the substance to additionally provide an adhesive attachment between the strip and the surface to hold the delivery system in place. Treatment agent 14 in FIG. 1 is an illustration of one adhesive agent.

All three Sagel et al patents provide for covering the front of the teeth but do not have a configuration suitable for covering the back of the teeth.

One embodiment of the present invention is to provide a simple method and device for whitening teeth could be provided.

Another embodiment is a method and device that uses commonly known dental materials.

Yet another embodiment is a method and device that is low cost and yet effective.

Still another embodiment profices a device that can be reused by the same patient simply by rinsing and cleaning the tray.

One embodiment is a dental bleaching tray that can also be used for other purposes, such as fluoride treatment, anti-bacterial treatments and the like.

Other embodiments will appear hereinafter.

SUMMARY OF THE INVENTION

The present invention is an assembly of two components, referred to as the upper and lower jaw pattern forms. Pattern forms are sized to generally allow the device to generally conform to the patient's teeth. Both the upper jaw and lower jaw patterns are die cut from commercially available dental wax, and are formed into specific patterns with fold lines impressed thereon to permit the pattern to be folded into a three dimensional tray when contoured to teeth along those fold lines.

The term "dental wax" is well known in the art and describes a large number of products of various compositions and components, all of which are known by this generic term. The preferred wax is paraffin wax, and the preferred dental waxes of the present invention contain at least 25 percent by weight of paraffin wax, and preferably over 40 percent by weight paraffin wax. Other components may be resins such as polyvinyl acetate and other synthetic resins that are compatible with the human body, in that they do not have a harmful affect on the user. One preferred dental wax is manufactured by Hase Petroleum Wax Co. of Arlington Heights, Ill., and is sold under the trade name HP 11168 dental wax. This preferred dental wax has a melting point of between about 140° F. and 160° F., and softens at less than 98° F. so that it can be used as described herein.

The dental wax used is thin, ranging from about 0.02 to 0.08 inches thick, with 0.04 inch thickness being preferred. The wax is capable of softening at body temperature, of less than 98.6° F., and is contoured by being held between the user's fingers and thumb before being placed on the teeth for forming.

The finished tray is then removed and bleaching solutions are placed in the tray. In this embodiment the inside of the tray adjacent to the teeth is textured or scoreds to hold the solution. Other solutions can also be used with this tray, such as fluoride treatment, anti-bacterial treatments and the like.

The invention provides a simple dental tray that is easily and inexpensively made without the necessities of repeat visits to a dentist or doctor, and without the necessity of sophisticated equipment or technicians.

DETAILED DESCRIPTION OF THE INVENTION

Figure 1:
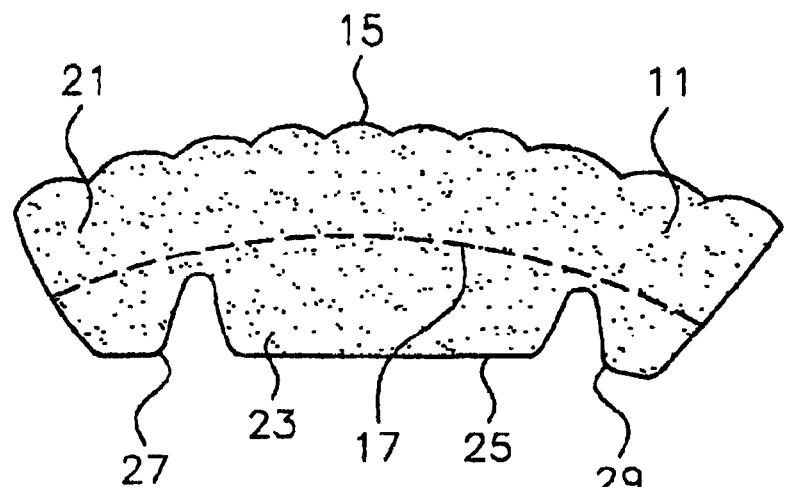
FIG. 1 is side elevational view of the lower jaw pattern of the present invention.
Figure 2:
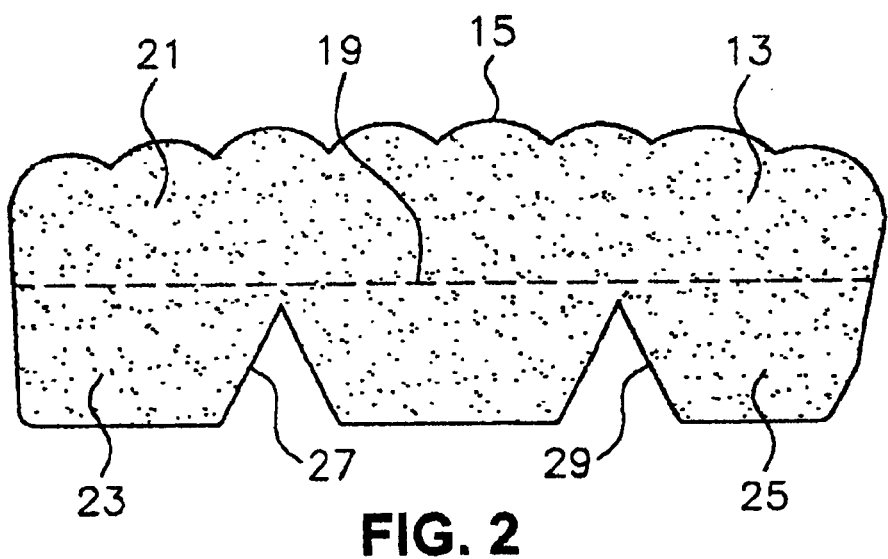
FIG. 2 is side elevational view of the upper jaw pattern of the present invention.

As shown in the drawings, the present invention comprises a thin dental wax pattern that can be folded to form a bleaching tray. A lower jaw pattern 11 is shown in FIG. 1 and an upper jaw pattern 13 is shown in FIG. 2. Both the lower pattern 11 and the upper pattern 13 have a front edge 15 which is sized to cover the front of a user's teeth.

Both patterns 11 and 13 also have a longitudinal fold line 17 and 19, respectively, which divide the patterns 11 and 13 into two parts, the front portion 21 that extends from fold line 17 in FIG. 1 or fold line 19 in FIG. 2, to front edge 15 and the back portion 23 that extends from fold line 17 to back edge 25. Back portion 23 has at least two areas 27 and 29 cut from the back portion, extending generally from the back edge 25 to fold line 17, to permit the pattern to be folded to form a tray conforming to the patient's lower or upper teeth.

In the lower jaw pattern shown in FIG. 1, the fold line 17 and the front edge 15 are arcuate, defining a curve that permits better conformation to the lower jaw. In FIG. 2, it is seen that the fold line 19 is straight and axial with the length of the pattern 13, and front edge 15 has a lesser arcuate curve.

As noted above, the dental wax is thin, ranging from about 0.02 to 0.08 inches thick, with 0.04 inch thickness being preferred. The wax is capable of softening at body temperature, of less than 98.6° F., and is contoured by being held between the user's fingers and thumb before being placed on the teeth for forming. Another way of warming the wax for application is to simply hold it under the warm water tap while running the warm water for a few minutes. One preferred dental wax is the previously described Hase Petroleum Wax Co. dental wax HP 11168.

It should be noted that the tray of the present invention is capable of covering the entire set of teeth up to the gum line or gingival margin. Once the tray is warm, it is placed against the front of the teeth and folded over the teeth to extend over the back of the teeth. Finger pressure is used to pack the tray against the front and back, and then the jaw is closed to bite gently, to replicate the tops of the teeth as well. Thus a total treatment of all the teeth, or any region of the upper or lower teeth, can effectively be achieved. Finally, the top of the tray can be trimmed with scissors or a hot instrument, and then flame polished to eliminate any sharp edges.

The finished tray that has been formed to fit the user is then removed and bleaching solutions are placed in the tray. The inside of the tray is textured, such as by pressing during the cutting stage during manufacture, to hold the bleaching solution. Preferred bleaching solutions and other solutions that affect the appearance of the teeth are, without limitation, hydrogen peroxide, carbamide peroxide, sodium fluoride, sodium monofluorophosphate, pyrophosphate, clorhexidine, polyphosphate, triclosan and enzymes. One preferred treatment agent is a chlor-haidine solution used as an antibacterial agent for the treatment of gingivitis. Another preferred treatment agent is potassium nitrate for the treatment of tooth sensitivity.

As has been noted above, the present invention may be used for bleaching but other dental procedures are also within the scope of the invention, including whitening, stain bleaching, stain removal, remineralization, plaque removal and tartar removal. It is contemplated that the tray of the present invention will cover all or only some of the patient's teeth, depending on the treatment in use. Simple cosmetic bleaching often does not include any teeth that are not visible in normal smiling and the like, such as those back from the first bicuspid.

The tray is now ready for use. A number of tests were performed, using the present invention, producing a whitening or bleaching of the teeth of a number of individuals, with results being substantially identical to bleaching procedures done by dentists and dental hygienists in the dental offices. The cost of using the invention described herein is much less than that of a dental office.

While particular embodiments of the present invention have been illustrated and described, it is not intended to limit the invention, except as defined by the following claims.

What is claimed is:

1. A method for treating at least some of a patient's teeth, comprising the steps of:

forming a pattern from dental wax, said pattern having a length sufficient to cover the selected patient's teeth on one jaw and a height twice the nominal length of the selected patient's teeth on said one jaw, said wax having a softening temperature of less than 98.6° F.; and folding said pattern along a longitudinal fold dividing said pattern into a front portion sized to cover said teeth on said one jaw and a back portion to form a tray shaped device for covering said teeth on said one jaw, said pattern including at least two cut-out areas in said back portion to permit said pattern to be folded to form a tray conforming to the patient's teeth, said dental wax being sufficiently deformable at room temperature to permit a patient to conform said tray to said teeth on said one jaw.

2. The method of claim 1, wherein said pattern is sized to cover the teeth on the lower jaw of a patient, said fold and said front portion defining a curve that permits conformation of said front portion to said lower jaw.

3. The method of claim 1, wherein said pattern is sized to cover the teeth on the upper jaw of a patient, said line being straight and axial with the length of the pattern, and said front edge has a slight arcuate curve that permits conformation of said front portion to said upper jaw.

4. The method of claim 3, wherein said dental wax pattern is about 0.04 inch in thickness, and said dental wax comprises a wax having at least 40% by weight paraffin wax.

5. A tray device for use in treating at least some of a patient's teeth, comprising:

a pattern formed from dental wax, said pattern having a length sufficient to cover the selected patient's teeth on one jaw and a height twice the nominal length of the selected patient's teeth on said one jaw, said wax having a softening temperature of less than 98.6° F.; and a longitudinal fold dividing said pattern into a front portion sized to cover said teeth on said one jaw and a back portion to form a tray shaped device for covering said selected teeth on said one jaw, said pattern including at least two cut-out areas in said back portion to permit said pattern to be folded to form a tray conforming to the patient's teeth, said dental wax being sufficiently deformable at room temperature to permit a patient to conform said tray to said teeth on said one jaw.

6. The device of claim 5, wherein said pattern is sized to cover the teeth on the lower jaw of a patient.

7. The device of claim 6, wherein said fold and said front portion are arcuate, defining a curve that permits conformation of said front portion to said lower jaw.

8. The device of claim 5, wherein said pattern is sized to cover the teeth on the upper jaw of a patient.

9. The device of claim 8, wherein said fold is straight and axial with the length of the pattern, and includes a front edge having a slight arcuate curve that permits conformation of said front portion to said upper jaw.

10. The device of claim 5, wherein said dental wax pattern is thin, ranging from about 0.02 to 0.08 inches thick.

11. The device of claim 10, wherein said dental wax pattern is about 0.04 inch in thickness.

12. The device of claim 11, wherein said dental wax comprises a wax having at least 40% by weight paraffin wax.

13. The device of claim 5, wherein said pattern is sized and trimmed to cover the entire teeth selected for treatment, including the back of the teeth to the gingival margin.

14. The device of claim 13, wherein said tray is trimmed after forming.

15. The device of claim 5, wherein said dental wax pattern scored on the side to be in contact with the teeth being treated.

16. A tray device for use in treating at least some of a patient's teeth, comprising:

pattern means formed from dental wax for covering the selected patient's teeth on one jaw, said pattern means having a height twice the nominal length of the selected patient's teeth on said one jaw, said wax having a softening temperature of less than 98.6° F.; and longitudinal fold means for dividing said pattern means into front portion means for covering said teeth on said one jaw and back portion means for forming a tray shaped device for covering said teeth on said one jaw, said pattern means including at least two cut-out areas in said back portion to permit said pattern means to be folded to form a tray conforming to the patient's teeth, said dental wax being sufficiently deformable at room temperature to permit a patient to conform said device to said teeth on said one jaw.

17. The device of claim 16, wherein said pattern means is sized to cover the teeth on the lower jaw of a patient.

18. The device of claim 17, wherein said fold means and said front portion means are arcuate, defining a curve that permits conformation of said front portion means to said lower jaw.

19. The device of claim 16, wherein said pattern means is sized to cover the teeth on the upper jaw of a patient.

20. The device of claim 19, wherein said fold means is straight and axial with the length of said pattern means, and said front portion means has a slight arcuate curve that permits conformation of said front portion means to said upper jaw.

21. The device of claim 16, wherein said dental wax pattern means is thin, ranging from about 0.02 to 0.08 inches thick.

22. The device of claim 21, wherein said dental wax pattern means is about 0.04 inch in thickness.

23. The device of claim 16, wherein said dental wax comprises a wax having at least 40% by weight paraffin wax.

24. The device of claim 16, wherein said pattern is sized and trimmed to cover the entire teeth selected for treatment, including the back of the teeth to the gingival margin.

25. The device of claim 24, wherein said tray is trimmed after forming.

26. The device of claim 16, wherein said dental wax pattern scored on the side to be in contact with the teeth being treated.

* * * * *